United States Patent [19]

Sulyok et al.

[11] Patent Number: 5,753,695
[45] Date of Patent: May 19, 1998

[54] FLAVILIUM COMPOUNDS AND METHOD OF USING

[75] Inventors: György Sulyok; János Bálint; Ildikó Borbély; Jolán Kiss; Ferenc D. Tóth, all of Debrecen, Hungary

[73] Assignee: Biogal Gyogyszergyár RT, Hungary

[21] Appl. No.: 252,941

[22] Filed: May 19, 1994

[30] Foreign Application Priority Data

Sep. 21, 1992 [HU] Hungary ................ P9203000

[51] Int. Cl.$^6$ ................ C07D 311/04; A61K 31/35
[52] U.S. Cl. ................ 514/456; 514/885; 549/405; 549/406
[58] Field of Search ................ 549/405, 406; 514/456, 885

[56] References Cited

U.S. PATENT DOCUMENTS

| | | | |
|---|---|---|---|
| 3,266,903 | 8/1966 | Jurd | 549/406 |
| 3,617,268 | 11/1971 | Murakami et al. | 549/406 |
| 4,105,675 | 8/1978 | Iacobucci et al. | 549/406 |
| 4,258,055 | 3/1981 | Lietti et al. | 549/406 |

FOREIGN PATENT DOCUMENTS 1904810  10/1969  Germany.

OTHER PUBLICATIONS

Baranac et al., CA 112:197949 (1990), registry No. 20921-31-7.

Baranac et al., CA 112:118124 (1990), registry No. 20931-21-9 amd 83615-98-9.

Baranac et al., CA 107:115077 (1987), registry No. 1222-48-6, 4082-08-0 and 20921-31-7.

Gavrilyuk et al., CA 99:196625 (1983), registry No. 30463-83-3.

Horie et al., CA 99:131343 (1983), registry No. 30463-83-3.

O'Neill et al., CA 98:68685 (1983), registry No. 4082-08-0.

Timberlake et al., CA 87:150302 (1977), registry No. 1090-74-0 and 20931-18-4.

Nekhoroshev et al., CA 87:117749 (1977), registry No. 63960-01-0.

Busetta et al., CA 81:42658 (1974), registry No. 53062-79-6.

Timberlake et al., CA 72:43454 (1970), registry No. 20921-31-7, 20931-18-4, 20931-21-9, 26091-45-2 and 26091-50-9.

Timberlake et al., CA 70:11494 (1969), registry No. 20921-31-7, 20931-18-4, 20931-21-9.

Bendz et al., CA 67:64180 (1967), registry No. 4082-08-0.

Bendz et al., CA 67:64180 (1967), registry No. 4134-79-6.

Kokkinos et al., CA 79:114730 (1973), registry No. 6587-05-9.

Jurd, CA 66:2439 (1967), registry No. 6587-04-8.

Murakami et al., CA 71:3277 (1969), registry No. 6587-03-7.

Harper et al., CA 66:101939 (1967), registry No. 6845-96-1.

Bendz et al., CA 67:64180 (1967), registry No. 15402,17-2.

Harper et al., CA 66:101939 (1967), registry No. 15896-53-4.

Harper et al., CA 66:101939 (1967), registry No. 15896-50-1.

Jurd, CA 71:29862 (1969), registry No. 24531-81-5.

Timberlake et al., CA 68:28493 (1968), registry No. 1151-98-0.

Bate-Smith et al., CA 67:8699 (1967), registry No. 1154-78-5.

Huff, Journal of Medicinal Chemistry, Aug. 1991, vol. 34, No. 8, pp. 2305-2314.

CA120:153045 Mahmood, (Antiviral Res. (1993), 22 (2-3), 189-99;CA119:111945 Tao, (Zhongguo Yixue Kexueyuan Xuebao (1992), 14(5), 334-8);CA119:62454 Nakashima, (Antiviral Res. (1992), 18(1), 91-103); CA119:314 Kilkuskie, (Bioorg. Med. Chem. Lett. (1992), 2(12), 1529-34; CA117:245072 Moore, (Biochem. J. (1994), 2 88(3), 717-19); CA117:204523 Ono, (Eur. J. Biochem., (1991), 199(3), 769); CA114:240605 Nonaka, (PCT WO 9004968, May 17, 1990); CA113:163 Ono, (Eur. J. Biochem., 1990, 190(3), 469-76); CA110:147191 Take, (J. Antibiot. (1989), 42(1), 107-115).

*Primary Examiner*—R. W. Ramsuer

*Assistant Examiner*—Laura L. Stockton
*Attorney, Agent, or Firm*—Schweitzer Cornman Gross & Bondell LLP

[57] ABSTRACT

The invention relates to a compound of formula (I)

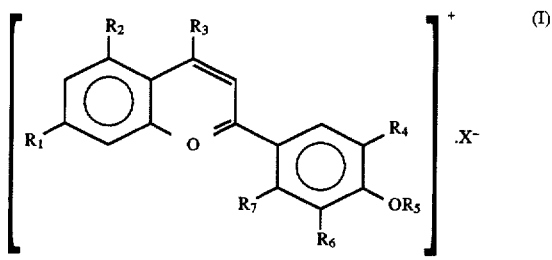

wherein

X is a pharmacologically acceptable anion, $R_1$ and $R_2$ are independently of each other hydrogen, or an —OY group in which Y is hydrogen, an α-aminoacyl, or a $C_{1-5}$ aminoalkyl residue, $R_3$, $R_4$ and $R_7$ are independently of each other hydrogen, or a $C_{1-5}$ alkyl residue $R_5$ is hydrogen, and α-aminoacyl, or a $C_{1-5}$ alkyl residue, and $R_6$ is hydrogen, OH⁻, or a $C_{1-5}$ alkyl residue, and pharmaceutically acceptable salts and esters thereof; and to condensation processes for preparing them.

1 Claim, 1 Drawing Sheet

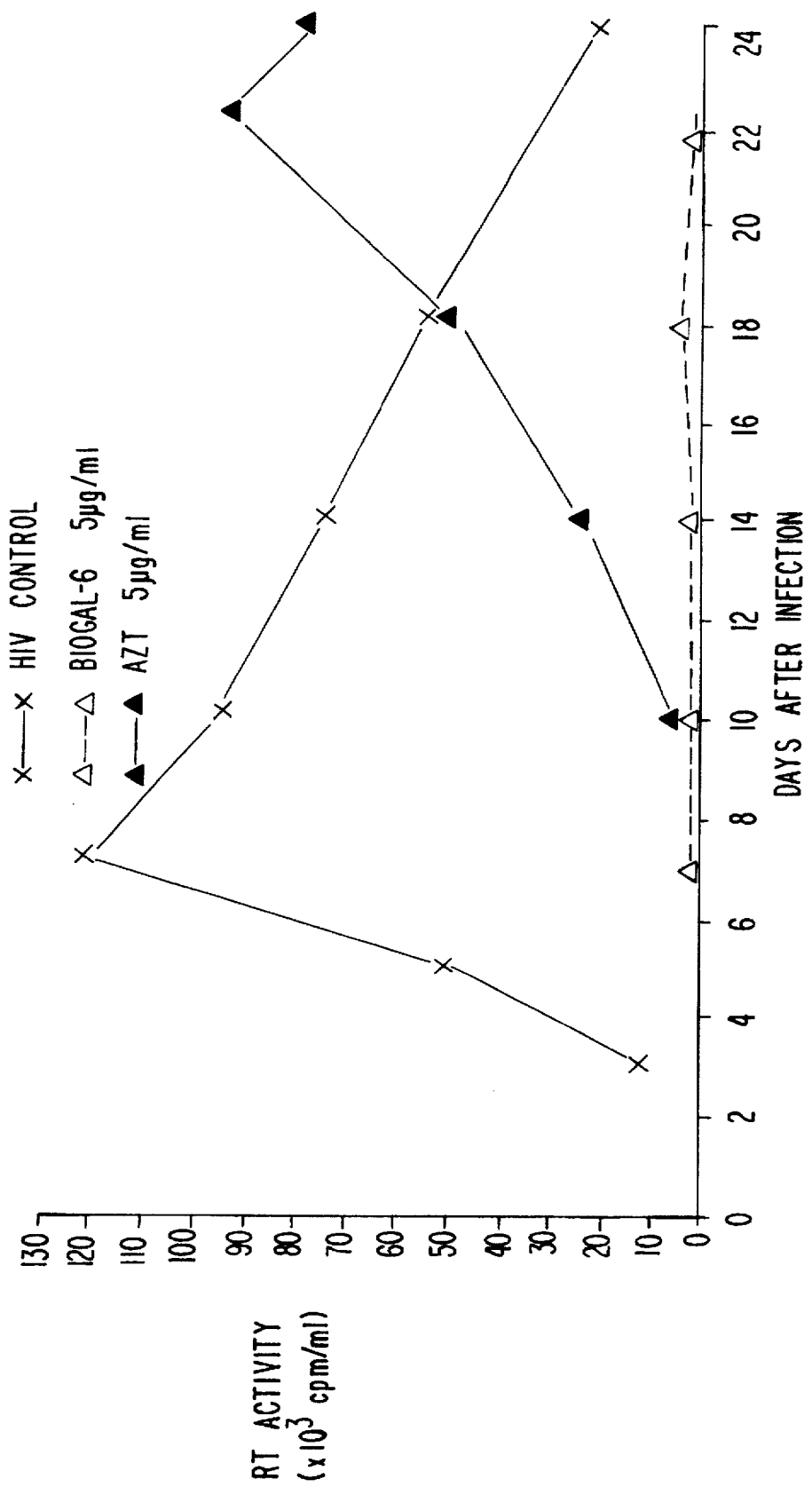

FLAVILIUM COMPOUNDS AND METHOD OF USING

This application is a CIP of PCT/HU93/00052 filed Sep. 8, 1993 published as WO95/06787 Mar. 31, 1994.

FIELD OF THE INVENTION

The present invention relates to novel phenylbenzopyrillium salts that are flavilium derivatives.

BACKGROUND OF THE INVENTION

Flavonoids are well-known coloring substances of plants. Flavilium salts are a member of this family of compounds. These salts are widely used in the food industry such as for coloring fruits and other vegetable matter (e.g. German patent No. 1,904,810, East German patent No. 140,353, and U.S. Pat. No. 3,315,975).

Medical applications of flavilium derivatives, such as their lipid and cholesterol level decreasing effects are described in European patent No. 19,524, and German patent No. 2,808,820, and the effect of flavilium chloride which is similar to that of vitamin P is described in German patents Nos. 2,002,421 and 2,703,375.

Flavilium derivatives can be obtained from plants by various extraction methods or by synthetic procedures. According to one synthetic method a suitable phenol derivative is condensed with a substituted chalcone or phenyl-β-diketone, for examples as described in German patents Nos. 1,904,810 and 2,808,823, or a α-chloro-β-N,N-dimethyl-formimidoyl-styrene perchlorate is used as a condensation partner to produce 7-amino-flavilium salts, as described in East German patent No. 140,353.

According to other possible reactions the desired compounds can be prepared from a natural vegetable basic material by various reducing methods (Mg+sulfuric acid, LiAlH$_4$, Zn+acetic anhydride) (e.g. as described in German patents Nos. 2,002,421, and 2,703,375, European patent No. 19,524, and Japanese patent No. 55,036,679).

DESCRIPTION OF THE DRAWING

The invention is described by reference to the enclosed sole FIGURE diagrammatically comparing the effects of the present invention and a commercial compound and an HIV control.

DESCRIPTION OF THE INVENTION

The novel flavilium compounds of the present invention have the formula (I)

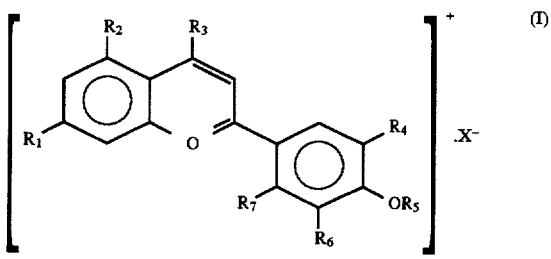

wherein

X is a pharmacologically acceptable anion;

$R_1$ and $R_2$ are independently of each other hydrogen or an —OY group in which Y is hydrogen, an α-amino-acyl, or a $C_{1-5}$ aminoalkyl residue;

$R_5$ is hydrogen, an α-aminoacyl, or $C_{1-5}$ aminoalkyl residue;

$R_3$, $R_4$, and $R_7$ are independently of each other hydrogen, or a $C_{1-5}$ alkyl residue; and $R_6$ is hydrogen, hydroxy, or a $C_{1-5}$ alkyl residue.

The $C_{1-5}$ alkyl residue is suitably a methyl, ethyl, propyl, isopropyl, n-butyl, sec-butyl tert-butyl, n-pentyl or isopentyl residue, most suitably methyl; and the α-aminoacyl residue can suitably be the acyl radical of an essential amino acid, most suitably a glicyl, alanyl, lysil, or arginyl residue.

Particularly suitable compounds of the present invention include 5,7,4'trihydroxy-4,3',4'trimethyl-flavilium salt, such as chloride, 5,7,4'-trihydroxy-4,3',5'-trimethyl-2-phenylbenzopyryllium chloride and 2-(4-hydroxy-3,5-dimethylphenyl)=5,7-dihydroxy-4-methyl-1-benzopyrillium chloride.

The compounds of formula (I) have an outstanding selective antiviral effect. Particularly important is their effect against the HIV virus. They proved to be more effective and less toxic than azidothymidine (AZT).

The compound of formula (I) can not be produced by known prior art methods, partly because the suitable vegetable starting material is frequently not available, and also because the methylated coumarin derivative and methylated phenol starting materials will under normal conditions generally not enter into a meaningful condensation reaction.

According to the Goswami-Chakravarti synthesis coumarin is condensed with resorcinol by heating the reactants in the presence a catalytic amount of phosphorus oxychloride (J. Ind. Chem. Soc. Vol. 9, p. 599, 1932).

We found that the compounds of formula (I) can be prepared in accordance with the present invention by condensing a phenol derivative of formula (II)

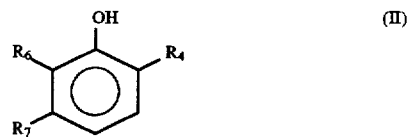

wherein $R_4$ $R_6$, and $R_7$ are as defined above, with a coumarin derivative of formula (III)

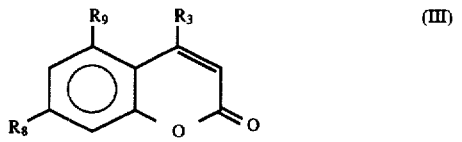

wherein $R_8$ and $R_9$ are hydrogen, or OH⁻; and $R_3$ is hydrogen, or a $C_{1-5}$ alkyl residue.

Condensation is suitably carried out in the presence of a much higher amount of phosphorous oxychloride than the amount used in the known Goswami-Chakravarti synthesis.

Suitably from about 1 to about 1.5 moles of phosphorus oxychloride based on the reactants is used. A Lewis acid, e.g. AlCl$_3$, or zinc chloride can also be used instead of phosphorus oxychloride. Condensation takes place at a temperature in the range of from about 70° C. to about 115° C. in the course of reaction.

Hydrochloric acid gas is suitably employed for an improved yield. In that case the reaction can also take place at room temperature.

Alternatively, compounds of formula (I) can be prepared in accordance with the present invention by condensing a phenol derivative of formula (V)

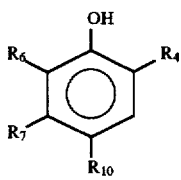

wherein $R_4$, $R_6$, and $R_7$ are as defined above; and $R_{10}$ is an acetoacetyl residue;

with a compound of formula (IV),

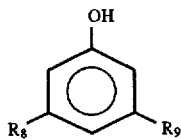

wherein $R_8$ and $R_9$ are as defined above.

Suitably the condensation is performed between about 15° C. and about 30° C., advantageously in the presence of hydrochloric acid gas.

In both of the above procedures the hydrochloride salt is separated and optionally a different pharmacologically accepted acid addition salt is prepared in a manner known per se.

If desired, the compound of formula (I) wherein either or both Y and $R_5$ are hydrogen, can be either (i) converted into an ester with an α-amino acid, or (ii) reacted with a $C_{1-5}$ aminoalkyl halide.

Esterification can be carried out e.g. by coupling the appropriate compound of formula (I) with an N-protected α-amino-acid, by a coupling agent such as dicyclohexylcarbodiimide. A conventional amino protecting group can be employed, such as a tert butoxycarbonyl group. The protecting group is to be removed by acidic treatment after the coupling reaction.

The HIV reverse transcriptase inhibiting activity of compounds of formula (I) of the invention was measured by the method of Hoffman, A. D. et al. described in Virology, Vol. 147, pp. 326–335, 1985.

The measurement results are shown for the model compound 5,7,4'-trihydroxy-4,3',5'-trimethyl-flavilium chloride (hereinafter referred to as "BIOGAL 6") and prepared as described in Example 1 below.

The active agents were tested on MT-4 and H9 human lymphocyte cell-lines infected with the strain HIV-1 IIIB. The cells were infected with 20 $TCID_{50}$ of the HIV-1 virus.

The active agents were tested in concentrations of 5, 20 and 100 µg/cm³. The active agent was first added to the culture 4 hours before the infection, and then 24, and 48 hours after infection. HIV infected, untreated MT-4 and H9 cells were used, as well as uninfected, untreated cells as a control. The AZT-control was zidovudine (ZDU) sold by Burroughs Wellcome Company under the name Retrovir.

Reverse transcriptase inhibiting activity was determined on 500 µl aliquots from supernatant of the culture and their virus concentration was measured. The results are given in cpm/cm³ indicating $^3$H-TTP.

Table 1 shows the activity level of reverse transcriptase inhibition on virus production. The activity was measured every 3–4 days, but Table 1 shows below only the representative results from the 7th, 10th, and 18th days.

TABLE 1

Comparison of effect of the BIOGAL 6 and AZT on HIV replication

| Active substance | Dose µg/cm³ | RT activity (cpm/cm³) | | |
|---|---|---|---|---|
| | | 7 day | 10 day | 18 day |
| BIOGAL 6 | 5 | 1.795 | 1.228 | 1.198 |
| | 20 | 1.748 | 1.626 | 1.300 |
| | 100 | 1.666 | 1.300 | 1.359 |
| AZT | 5 | 2.195 | 2.127 | 38.797 |
| | 20 | 2.386 | 2.224 | 1.921 |
| | 100 | 2.220 | 2.181 | 1.838 |
| HIV CONTROL | — | 113.000 | 84.000 | 28.211 |

BIOGAL-6 completely blocked the HIV replication at a concentration of 5 µg/cm³. AZT also suppressed HIV proliferation at a concentration of 5 µg/cm³, but this effect did not last as long as the effect of BIOGAL-6.

The effects of BIOGAL-6 and of AZT were further compared at the concentration levels of 5, 2.5, 1, 0.5, and 0.1 µg/cm³. Table 2 below summarizes representative results. One can see that BIOGAL-6 was completely ineffective at 1.0 µg/cm³ and below, however the effect of BIOGAL-6 at 2.5, and 5 µg/cm³ concentrations was long-lasting, while administration of AZT had only a temporary effect even at higher concentrations.

TABLE 2

Comparison of effects of BIOGAL-6 and AZT

| Active substance | Dose µg/cm³ | RT activity (cpm/cm³) | | |
|---|---|---|---|---|
| | | 7 day | 10 day | 18 day |
| BIOGAL 6 | 5.0 | 1.478 | 1.019 | 1.226 |
| | 2.5 | 6.231 | 8.938 | 6.803 |
| | 1.0 | 96.638 | 75.917 | 38.595 |
| | 0.5 | 108.846 | 98.150 | 43.804 |
| | 0.1 | 111.035 | 99.813 | 45.535 |
| AZT | 5.0 | 1.724 | 3.571 | 51.735 |
| | 2.5 | 3.231 | 9.083 | 116.001 |
| | 1.0 | 3.989 | 15.115 | 75.539 |
| | 0.5 | 6.148 | 75.051 | 84.047 |
| | 0.1 | 7.392 | 125.627 | 62.817 |
| HIV CONTROL | — | 122.970 | 95.047 | 59.260 |

As shown in FIG. 1, BIOGAL-6 completely blocked HIV production at a concentration of 5 µg/cm³, while AZT at the same concentration only delayed the HIV production but did not change the proliferation rate. The effect of BIOGAL-6 was long lasting when compared to AZT. This difference suggests that the two compounds exert their action through different mechanisms.

Acute toxicity examinations on CFP/SPF laboratory mice strains and WISTAR Charles River/SPF laboratory rat strains, orally and intravenously have shown that BIOGAL-6 is nontoxic at oral doses even as high as 2,000 µg/kg.

The invention is further illustrated by the following examples.

EXAMPLE 1

Preparation of 5,7,4'-trihydroxy-4,3',5'-trimethyl-flavilium chloride (BIOGAL-6)

4-methyl-5,7-dihydroxy-coumarin (3.842 g) and 2,6-dimethyl-phenol (2.44 g) are boiled under reflux in the presence of 10 cm³ of $POCl_3$, and 3 g of $ZnCl_2$ at 100° C. for 30 minutes. The mixture is then poured into 200 cm³ of ice water. The precipitate is dissolved in 100 cm³ methanol and the solution is treated with 3 dm³ ethyl acetate. The precipitate is filtered off, dissolved in methanol and chromatographed on an adsorbent charge of Fractogel PGM 2000. The eluted material is recovered under reduced pressure at 60° C. in a rotary evaporator. The separation with ethyl acetate and the chromatographic purification steps are repeated if necessary. The orange-yellow compound was analyzed $R_f$: 0.58 Merck cellulose (5632) water: hydrochloric acid: acetic acid=3:2:5 v/v ¹H NMR (200 MH; $DMSO_{d6}$-δ(ppm): 2.25 (s,6H,2CH₃); 2.96 (s,3H,1CH₃); 6.80 (d,1H,CH—H6); 6.93 (d,1H,CH—H8); 8.0 (s,2H,CH—H2',H6'); 8.03 (s,1H, CH—H3)

EXAMPLE 2

Preparation of 5,7,4'-trihydroxy-4,3',5'-trimethyl-flavilium chloride (BIOGAL-6)

4 g 2,5-dimethyl-4-acetoacetyl-phenol and 4 g phloroglucinol are dissolved in 80 ml of water-free ethyl alcohol then hydrochloric acid gas is introduced and the solution is stirred at room temperature. Progress of the reaction is followed by thin layer chromatography. When ring-closure is finished within approximately 8 hours the reaction mixture is poured into water, the resulting precipitate is filtered off, and purified by column chromatography. The yield is 4.23 g. The product identification parameters are the same as described in Example 1.

EXAMPLE 3

Preparation of 4',5,7-trihydroxy-4,3',5'-trimethyl-flavilium chloride-5,7-dialanyl ester 1.3 g of the compound prepared according to Example 1 is reacted with 1.5 g of N-tert butoxycarbonyl-alanine in the presence of 1.6 g dicyclohexyl-carbodiimide. At the end of the reaction the precipitated dicyclohexyl urea is filtered off, the solvent is removed from the filtrate and the residue is dissolved in ethyl acetate. The solution is evaporated again and the title product is obtained after removing the protecting group by acidic treatment. The yield is 1.6 g of the title compound.

We claim:

1. A method for treating an animal host infected with HIV, which comprises administering to the host a pharmacological preparation containing as an active ingredient a compound of formula (I)

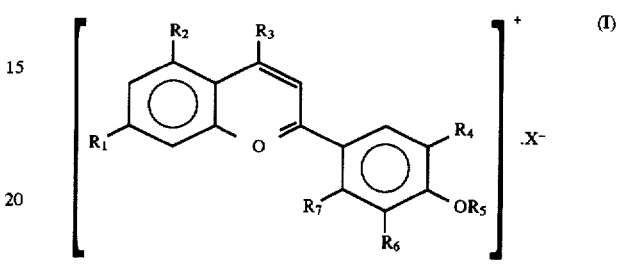

wherein

X is a pharmacologically acceptable anion, $R_1$ and $R_2$ are independently of each other an —OY group in which Y is hydrogen, an α-aminoacyl, or a $C_{1-5}$ aminoalkyl residue, $R_3$ is a $C_{1-5}$ alkyl residue, $R_4$ and $R_7$ are independently of each other hydrogen, or a $C_{1-5}$ alkyl residue, with the proviso that one of the two of $R_4$ and $R_7$ is other than hydrogen, $R_5$ is hydrogen, $R_6$ is hydrogen, OH⁻, or a $C_{1-5}$ alkyl residue, or pharmaceutically acceptable salt or ester thereof.

* * * * *